United States Patent

Beers et al.

[11] Patent Number: 5,994,563
[45] Date of Patent: Nov. 30, 1999

[54] ARYLMETHYLPHOSPHONIC ACID DERIVATIVES USEFUL IN TREATING BONE WASTING DISEASES

[75] Inventors: Scott Beers, Flemington; Roger F. Frechette, Somerville; Elizabeth A. Malloy, Flemington, all of N.J.; Charles Schwender, Dover, Mass.; Wei Wu, Somerville, N.J.

[73] Assignee: Ortho Pharmaceutical Corporation, Raritan, N.J.

[21] Appl. No.: 09/234,800

[22] Filed: Jan. 19, 1999

Related U.S. Application Data

[62] Division of application No. 08/831,987, Apr. 1, 1997, abandoned.

[51] Int. Cl.[6] .................... C07D 333/00; C07D 333/38; C07D 333/08; C07F 9/02
[52] U.S. Cl. .................... 549/6; 549/61; 549/68; 549/81; 558/214
[58] Field of Search .................... 549/6, 61, 68, 549/81; 558/214

[56] References Cited

U.S. PATENT DOCUMENTS 5,412,141   5/1995   Nugent ..................... 558/214
5,508,273   4/1996   Beers et al. ................ 514/141

*Primary Examiner*—Johann Richter
*Assistant Examiner*—Joseph Murray
*Attorney, Agent, or Firm*—Ralph Palo

[57] ABSTRACT

Benzyl-phosphonate compounds represented by the formula I:

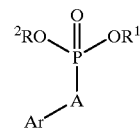

are disclosed as useful in treating bone wasting diseases and as an immunosuppresant.

13 Claims, No Drawings

ARYLMETHYLPHOSPHONIC ACID DERIVATIVES USEFUL IN TREATING BONE WASTING DISEASES

This is a Divisional of application Ser. No. 08/831,987, filed Apr. 1, 1997, now abandoned.

BACKGROUND OF THE INVENTION

Osteoporosis is a bone-wasting disease in which there is an imbalance or uncoupling between the rate of bone formation and resorption resulting in a decrease in total bone mass. As a result of this decrease in bone mass the skeleton becomes weakened and unable to bear the normal weight-bearing stresses. The effects of osteoporosis are generally seen in the weight-bearing bearing parts of the skeleton, especially the spine and hips, which can frature in the absence of trauma. Osteoporosis affects about 24 million people in the United States and 200 million people worldwide and is blamed for 2.5 million fractures a year in elderly women. The American Medical Association estimates that as many as 25% of women will suffer fractures of the hip or spine in their lifetime as a result of osteoporosis.

The current therapies for postmenopausal osteoporosis consist of treatments which are for the most part preventive; estrogen replacement, bisphosphonates, vitamin D metabolites and calcium supplements act to inhibit bone resorption associated with the onset of menopause. Estrogen replacement in these patients is quite effective in reducing further loss of bone mass but it does not induce an increase in bone mass which is needed to reduce fracture risk and pain. These treatments have little utility in the treatment of those patients with existing osteoporosis-induced loss of bone mass who have a high fracture risk and back/joint pain. Postmenopausal women with vertebral bone mass of less than 100 mg/cc would be considered below the "fracture threshold" and would be candidates for treatment with an agent which would increase bone mass and thereby restore lost bone. The present invention focuses on agents which are useful in treating bone wasting diseases by increasing an individuals bone mass and thus reducing fracture risk. The therapeutic need for this type of agent is clearly present, especially when one considers the poor patient compliance associated with estrogen replacement therapies. Modification of the immune system by pharmacologic agents is also rapidly emerging as a major area of therapeutics. While organ transplantation alone extends the lives of thousands of patients per year, disease such as diabetes mellitus, rheumatoid arthritis, multiple sclerosis and psoriasis affect millions more and have been shown to involve reactions to autoantigens. A role for immunosuppressive agents has not only been recognized in these cases but approved for therapy as well. These include Cyclosporine, FK-506, Azathioprine, adrenocorticosteroids and Methotrexate. These drugs all have serious toxicities associated with them such as renal toxicity (Cyclosporine, FK-506), leukopenia, thrombocytopenia (Azathioprine), hepatic fibrosis and cirrhosis (methotrexate) and psychoses, cataracts, glucose intolerance, bone dissolution (Adrenocorticosteroids). Clearly a need exists for an orally active specific inhibitor of T-cell function. The present invention describes agents which inhibit a crucial enzyme unique to T-cells (CD-45) and thus provide a more specific and less toxic approach to immunosuppression.

The assignees of the present invention recently filed an application Ser. No. 732,267 directed to certain novel benzylphosphonates. Such compounds were shown to have activity in treating bone wasting diseases. They are, however, structurally different from the compounds of the present invention.

SUMMARY OF THE INVENTION

Accordingly, the present invention is directed to benzylphosphonate compounds represented by the general formula I:

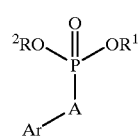

wherein $R^1$, $R^2$, A, and Ar are defined hereinafter, which compounds have been found to have utility in enhancing osteoblast cell proliferation thereby having utility in treating bone fractures and bone wasting diseases including osteoporosis through enhancement of bone calcification and have been found to have activity. The invention is also directed to Dharmaceutical compositions containing the compounds of formula I and methods of treating bone wasting and immune related diseases.

DETAILED DESCRIPTION OF THE INVENTION

More particularly, the present invention is directed to compounds represented by the formula I:

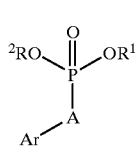

Ar is selected from any of phenyl, 2-thienyl or 3-thienyl. When Ar is phenyl it may be substituted with either of X or Y. Ar may also be substituted with Z Most preferably Ar is phenyl.

X and Y are selected from any of H, halo, azido, phenyl, $O(CH_2)_nR^3$, $S(O)_m(CH_2)_nR^3$, or $CH_2(CH_2)_nR^3$ wherein m=0–2, n=0–14, $R^3$=H, $C_1$–$C_4$alkyl, $C_3$–$C_{10}$ cycloalkyl, pyridyl, aryl such as phenyl or naphthyl, substituted aryl wherein the aryl substituents are selected from any of $C_1$–$C_8$ alkyl, halo, carboxy, $C_1$–$C_4$ carboalkoxy, $C_{1-C4}$ alkoxy, benzo, cyano, hydroxy, phenyl, phenoxy, nitro or trifluoromethyl. When Ar is phenyl, X is at the 2-position and Y is at the 4-position.

Z is selected from any of H, $C_1$–$C_4$ alkyl, $C_1$–$C_4$ alkoxy, cyano, halo, nitro, or trifluoromethyl. Z is most preferably nitro. Z occupies the 5-position when Ar is phenyl, the 4 or 5-position when Ar is 2-thienyl and the 5-position when Ar is 3-thienyl. The following formula shows the X, Y and Z substitution pattern on a compound of the present invention:

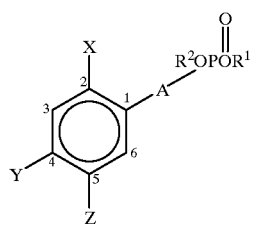

$R^1$ and $R^2$ are independently selected from any of H, $C_1-C_4$ alkyl, aralkyl, wherein the alkyl portion has 1–4 carbon atoms, substituted aralkyl wherein the aryl portion is independently substituted with halo, nitro, $C_1-C_4$ alkoxy or $C_1-C_4$ alkyl, $C_1-C_4$ alkylsulfonyl, phenylsulfonyl, substituted-phenylsulfonyl wherein the phenyl is independently substituted with any of $C_1-C_4$ alkyl or halo, $NR^3R^4$ wherein $R^3$ and $R^4$ are the same or different and are selected from either of H or $C_1-C_4$ alkyl. Most preferably, $R^1$ and $R^2$ are both H.

A is selected from any of $CHOR^5$ OR $C=O$ wherein $R^5$ is H, $C_1-C_4$ alkyl, $C_1-C_6$ acyl such as acetyl or pivaloyl, benzoyl or substituted benzoyl wherein the substituents are any of halo or $C_1-C_4$ alkyl.

As used herein, unless otherwise noted alkyl and alkoxy whether used alone or part of a substituent group, include straight and branched chains. For example, alkyl radicals include methyl, ethyl, propyl, isopropyl, n-butyl, isobutyl, sec-butyl, t-butyl, n-pentyl, 2-methyl-3-butyl, 1-methylbutyl, 2-methylbutyl, neopentyl, n-hexyl, 1-methylpentyl, 2-methylpentyl. Alkoxy radicals are oxygen ethers formed from the previously described straight or branched chain alkyl groups. Of course, if the alkyl or alkoxy substituent is branched there must be at least 3 carbon atoms.

The term "aryl" as used herein alone or in combination with other terms indicates aromatic hydrocarbon groups such as phenyl or naphthyl. The term "heteroaryl" means aromatic hydrocarbon groups containing 1 or 2 hetero atoms selected from any of S, O or N. With reference to substituents, the term independently means that when more than one of such substituent is possible such substituents may be the same or different from each other.

Racemates, individual enantiomers caused by the presence of a stereogenic carbon or phosphorus atom and diastereomers when both stereogenic carbon and phosphorus atoms are present are within the definition of formula I.

Representative salts of the compounds of formula I which may be used include pharmaceutically acceptable acidic salts made from organic and inorganic acids such as hydrochloric and hydrobromic, methanesulfonates and basic salts including ammonium, cyclohexylammonium, trisethanolammonium and salts of amino acids such as arginine and lysine as well as sodium, potassium, calcium, magnesium and the like. Such salts can be made by reacting the benzylphosphonic acids or esters of formula I with the appropriate agent and recovering the salt.

Particularly preferred compounds of the present invention include:
(2-Azido-5-nitro)phenylhydroxymethylphosphonic acid;
(2-Fluoro-5-nitro)phenylhydroxymethylphosphonic acid;
(2-Chloro-5-nitro) phenylhydroxymethylphosphonic acid;
(2-Methyl-5-nitro)phenylhydroxymethylphosphonic acid;
(2-Methoxy-5-nitro)phenylhydroxymethylphosphonic acid;
(2-Hydroxy-5-nitro)phenylhydroxymethylphosphonic acid;
[2-(2-Pyridylthio)-5-nitro]phenylhydroxymethylphosphonic acid;
(2-Phenylthio-5-nitro)phenylhydroxymethylphosphonic acid;
O,O-Diethyl-(2-cyclopentylthio-5-nitro)phenylhydroxymethyl phosphonate;
(2-Cyclopentylthio-5-nitro)phenylhydroxymethylphosphonic acid;
O,O-Diethyl-(2-cyclohexylthio-5-nitro)phenylhydroxymethyl phosphonate;
(2-Cyclohexylthio-5-nitro)phenylhydroxymethylphosphonic acid;
(2-Phenoxy-5-nitro)phenylhydroxymethylphosphonic acid;
(2-Benzylthio-5-nitro)phenylhydroxymethylphosphonic acid;
[2-(2-Methoxy)phenylthio-5-nitro]phenylhydroxymethylphosphonic acid;
[2-(4-Methyl)phenylthio-5-nitro]phenylhydroxymethylphosphonic acid;
[2-(4-T-butyl)phenoxy-5-nitro]phenylhydroxymethylphosphonic acid;
[2-(4-Methyl)phenoxy-5-nitro]phenylhydroxymethylphosphonic acid;
[2-(2-Methyl)phenoxy-5-nitro]phenylhydroxymethylphosphonic acid;
[2-(3-Methyl)phenoxy-5-nitro]phenylhydroxymethylphosphonic acid;
[2-(2,6-Dimethyl)phenoxy-5-nitro]phenylhydroxymethylphosphonic acid;
[2-(4-Trifluoromethyl)phenoxy-5-nitro]phenylhydroxymethylphosphonic acid;
[2-(4-Chloro)phenoxy-5-nitro]phenylhydroxymethylphosphonic acid;
[2-(4-Bromo)phenoxy-5-nitro]phenylhydroxymethylphosphonic acid;
[2-(3,4-Dimethyl)phenoxy-5-nitro]phenylhydroxymethylphosphonic acid;
[2-(4-Methylthio)phenoxy-5-nitro]phenylhydroxymethylphosphonic acid;
[2-(4-Cyano)phenoxy-5-nitro]phenylhydroxymethylphosphonic acid;
[2-(3-Cyano)phenoxy-5-nitro]phenylhydroxymethylphosphonic acid;
[2-(3-pyridyloxy)-5-nitro]phenylhydroxymethylphosphonic acid;
[2-(4-Chloro)phenylthio-5-nitro]phenylhydroxymethylphosphonic acid;
[2-(4-Methoxy)phenylthio-5-nitro]phenylhydroxymethylphosphonic acid;
[2-(4-t-Butyl)phenylthio-5-nitro]phenylhydroxymethylphosphonic acid;
[2-(3,4-Dimethoxy)phenylthio-5-nitro]phenylhydroxymethylphosphonic acid;
[2-(3-Methyl)phenylthio-5-nitro]phenylhydroxymethylphosphonic acid;
[2-(3-Chloro)phenylthio-5-nitro]phenylhydroxymethylphosphonic acid;
[2-(phenylpropyl)thio-5-nitro]phenylhydroxymethylphosphonic acid;
(2-cycloheptylthio-5-nitro)phenylhydroxymethylphosphonic acid;
[2-(2-naphthyl)thio-5-nitro]phenylhydroxymethylphosphonic acid;
O,O-Diethyl-[2-(4-acetamido)phenythio-5-nitro]phenylhydroxymethylphosphonate;
[2-(4-Acetamido)phenylthio-5-nitro]phenylhydroxymethylphosphonic acid;

[2-(3-Methoxy)phenylthio-5-nitro]phenylhydroxymethylphosphonic acid;
(2-decylthio-5-nitro)phenylhydroxymethylphosphonic acid;
(2-Phenyl-5-nitro)phenylhydroxymethylphosphonic acid;
[2-(3,5-Dichloro)phenylthio-5-nitro]phenylhydroxymethylphosphonic acid;
(2-Hexylthio-5-nitro)phenylhydroxymethylphosphonic acid;
[2-(2-Methylbenzylthio)-5-nitro]phenylhydroxymethylphosphonic acid;
[2-(3-Methylbenzylthio)-5-nitro]phenylhydroxymethylphosphonic acid;
[2-(4-Methylbenzylthio)-5-nitro]phenylhydroxymethylphosphonic acid;
[2-(4-Chlorobenzylthio)-5-nitro]phenylhydroxymethylphosphonic acid;
[2-(4-Fluorobenzylthio)-5-nitro]phenylhydroxymethylphosphonic acid;
[2-(Phenylethylthio)-5-nitro]phenylhydroxymethylphosphonic acid;
[2-(4-Methyl)phenylethylthio-5-nitro]phenylhydroxymethylphosphonic acid;
(2-n-Decylthio-5-nitro)phenylhydroxymethylphosphonic acid;
[2-(phenylpropylthio)-5-nitro]phenylhydroxymethyphosphonic acid;
(3-nitro-4-Chloro)phenylhydroxymethylphosphonic acid;
O,O-Diethyl-[3-nitro-4-(4-bromophenylthio)]phenylhydroxymethylphosphonate;
[3-Nitro-4-(4-bromophenylthio)]phenylhydroxymethylphosphonic acid;
O,O-Diethyl-[3-nitro-4-(3,4-dichlorobenzyloxy)]phenylhydroxymethylphosphonate;
[3-Nitro-4-(3,4-dichlorobenzyloxy)]phenylhydroxymethylphosphonic acid;
(3-Nitro-4-methyl)phenylhydroxymethylphosphonic acid;
(3-Nitro-4-chloro)phenylhydroxymethylphosphonic acid;
(3-Nitro-4-benzoyloxy)phenylhydroxymethylphosphonic acid;
[3-Nitro-4-(4-cyanophenoxy)]phenylhydroxymethylphosphonic acid;
(3-Nitro-4-methoxy) phenylhydroxymethylphosphonic acid;
(2-Chloro-5-nitro)phenyloxomethylphosphonic acid;
(2-Bromo-5-nitro)phenyloxomethylphosphonic acid;
(2-Chloro-4-nitro)phenyloxomethylphosphonic acid;
5-Nitro-2-thiophenehydroxymethylphosphonic acid;
4-Nitro-2-thiophenehydroxymethylphosphonic acid;
5-Nitro-3-thiophenehydroxymethylphosphonic acid;

The compounds of formula I may be prepared according to the following Schemes:

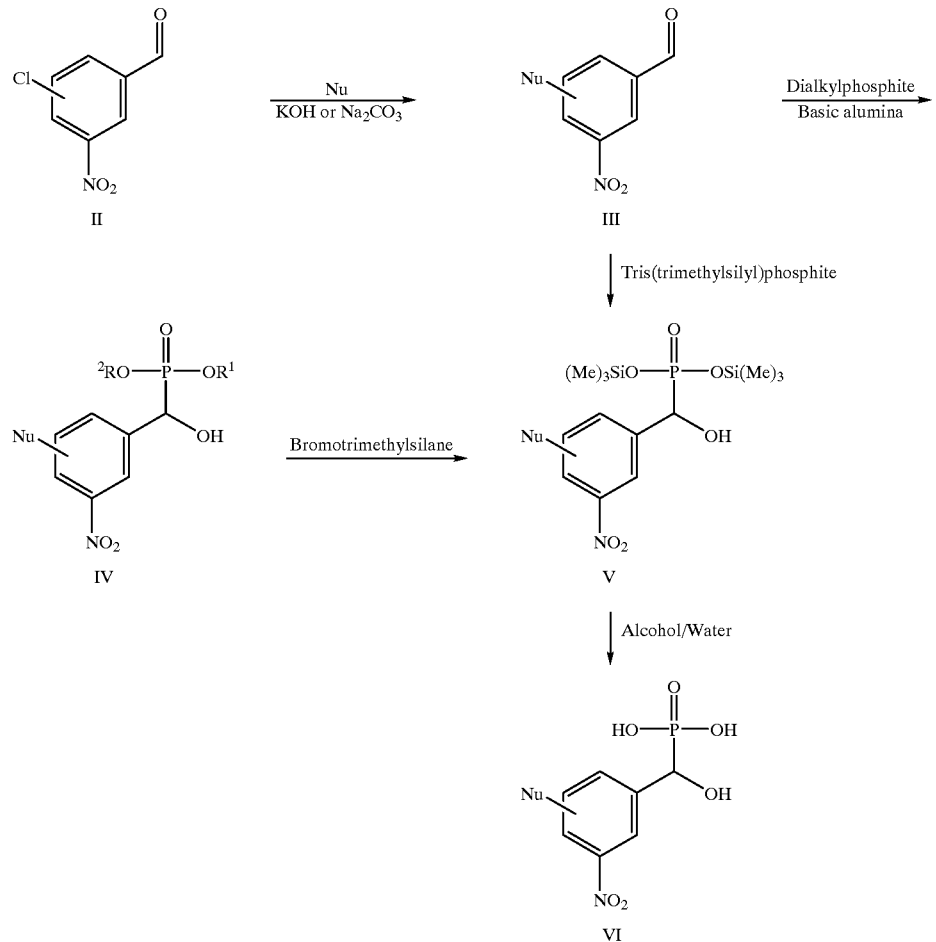

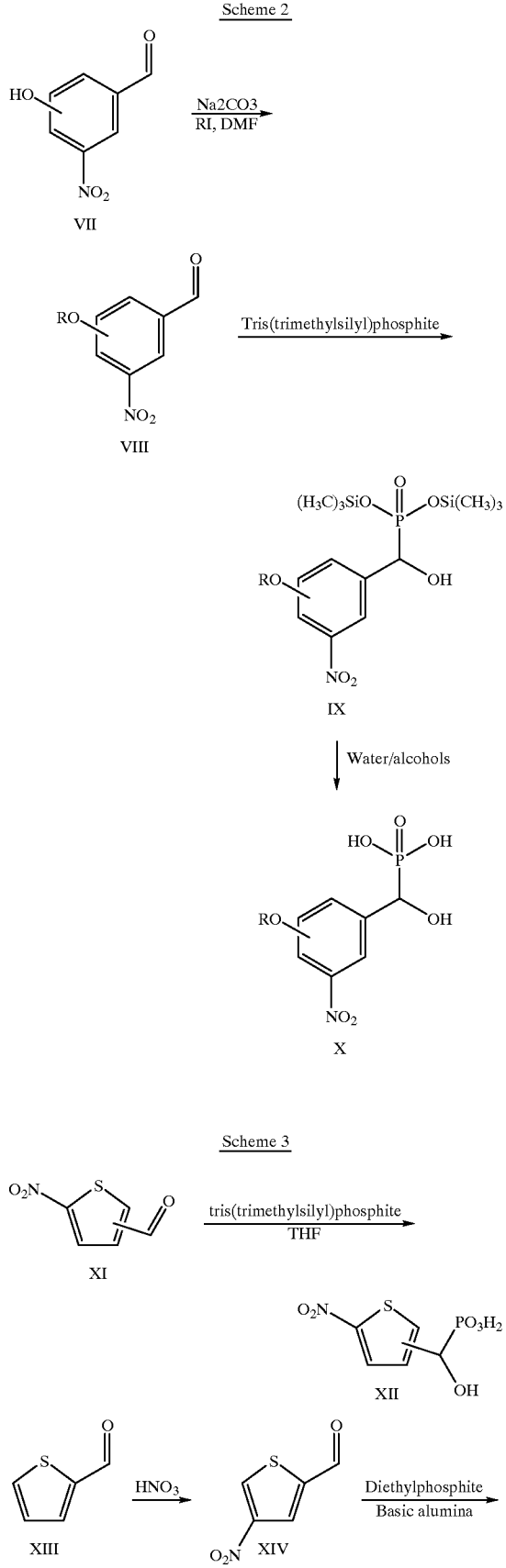

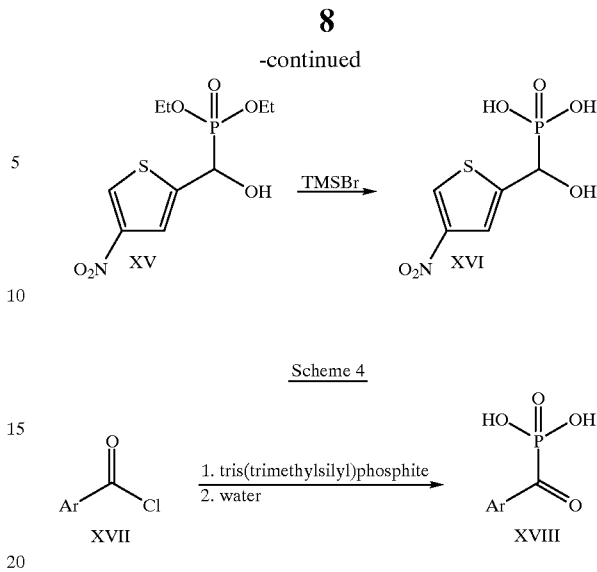

More specifically, as shown in Scheme 1, 2-Chloro-5-nitrobenzaldehyde or 4-Chloro-5-nitrobenzaldehyde (commercially available) can be reacted with the appropriate nucleophile (Nu) in dimethylformamide at 60–100°C. for 0.25–17 hours. The reaction mixture is poured into water and the product is either filtered or extracted with a suitable organic solvent such as ethyl acetate. The aldehyde, III, is used without further purification. The dialkylphosphonates, IV, are made by mixing III with the appropriate dialkylphosphite and adsorbing the mixture onto basic alumina. After 2–20 hours the product, IV, can be extracted with methylene chloride and purified if necessary with silica gel column chromatography. The trimethylsilyl esters, V, can be made either by treating IV with 4–8 molar equivalents of bromotrimethylsilane in an organic solvent such as methylene chloride or acetonitrile for 2–20 hours or by reacting Ill with tris(trimethylsilyl)phosphite in tetrahydrofuran for 2–20 hours. Compounds, VI, result from the treatment of V with water or an alcohol followed by crystallization or isolation as a salt.

As shown in Scheme 2, 2-hydroxy-5-nitrobenzaldehyde or 4-hydroxy-5-nitrobenzaldehyde, each of which are commercially available, can be reacted with 1–5 equivalents of the desired alkyl iodide and 2 equivalents of sodium carbonate in dimethylformamide at ambient temperature for 17–20 hours. The intermediate, VIII, is obtained using the workup procedure described for IV and reacted without further purification with tris(trimethyl-silyl)phosphite in tetrahydrofuran to give IX. Treatment of IX with water or an alcohol affords the target compound, X.

As shown in Scheme 3, 5-Nitro-2-thiophenecarboxaldehyde and 5-nitro-3-thiophene-carboxaldehyde, carboxaldehyde, each of which are commercially available, can be reacted with tris(trimethylsilyl) phosphite to give XII. Thiophene-2-carboxaldehyde is nitrated in sulfuric acid with potassium nitrate to give 4-nitrothiophene-2-carboxaldehyde which in turn is reacted with diethylphosphite on basic alumina and allowed to stand for 2–20 hours. Extraction of the product with methylene chloride gives XV. Treatment of XV with 5–8 equivalents of bromotrimethylsilane in methylene chloride ( 50–100 mL) gives compound XVI.

The appropriate aryl acid chloride, XVII is reacted with tris(trimethylsilyl) phosphite in a solvent such as tetrahydrofuran for 3–20 hours. Work up in the presence of water and/or alcohols gives the phenyloxomethyl series XVIII obtained as described for the preparation of VI.

In cases of this invention where A is equal to $OR^5$, the carbon directly attached to the phosphorous can exist in either the R or S configuration or as a mixture of both. Pure enantiomers of compounds VI, X and XVI can be obtained by performing the resolution with chiral amines such as the ephedrines, methylbenzylamine, amino acids and basic alkaloids such as quinidine and brucine. The resulting diastereomeric salts can be separated by fractional crystallization.

Compounds of the present invention have utility to treat bone fractures and bone wasting diseases including osteoporosis in animals including humans through enhancement of bone calcification. The compounds of the present invention have been evaluated as inhibitors of human osteoblastic (TE85) tyrosinephosphate phosphatase activity. Inhibitors of TE85 are involved with the stimulation of osteoblast cell proliferation in cell culture which is predictive of bone mass and bone formation in vivo. See, for example, K. H. Lau, H. Tanimoto and D. Baylink, *Endocrinology,* 1988, 123, 2858; L. K. Minor, M. Yang and K. D. Demarest, *J. Bone Min Res.* 1993, 8 (abstr 974)S360]; and K. T. Demarest, J. W. Gunnet, J. Jordan, L. K. Minor, and C. Schwender, *J. Bone Min. Res.* 1994, 9, B391.

Table 1 reports the results of the compounds of the present invention to inhibit TE85 and to stimulate osteoblast growth. Compounds of this invention are characterized by their $IC_{50}$ or concentration required to inhibit 50% of the TE85 enzyme reaction. Their ability to stimulate osteoblast proliferation at two concentrations, is presented in Table 1. Compounds wherein $R^1$ and $R^2$ are other than H are mono or diesters which exhibit a lower activity in vitro. However such compounds are useful as prodrugs of the acid ($R^1$ and $R^2$ equal H) and as intermediates useful in making the corresponding acid. Table 2 reports the results of the compounds of the present invention in the Enzyme Assay (CD45), which evidences their immunosuppresant activity Each of the assays and cell proliferation test will now be described.

Tyrosylphosphate Phosphatase Enzyme Inhibition Assay

Cells (human, osteoblast-line TE85) were rinsed, pelleted, rinsed and suspended in lysis buffer (25 mM Tris, pH 7.5, 25 mM sucrose, 0.1 mM EDTA, 5 mM MgCl, 5 mM DTT, and 10 ug/mL aprotinin and 10 ug/mL leupeptin). The cells were lysed by sonication and were centrifuged at low speed to remove cellular debris. The homogenate was centrifuged at 100,000×g for 1 hour. The supernatant is the cell cytosol and the pellet is the membrane fraction. These preparations are the sources of the enzyme. The substrate is a 14-amino acid peptide (Lys—Arg—Leu—lleu—Glu—Asp—Asn—Glu—Tyr—Ala—Ala—Arg—Gln—Gly) containing a single tyrosine residue that has been previously phosphorylated by Ick tyrosine kinase and $^{32}P$ labelled ATP. The tyrosylphosphatase reaction contains the $^{32}P$ peptide (0.1 uM), compound to be tested, an aliquot of the cellular extract, and 100 mM HEPES, pH 7.0 in a total volume of 100 uL. The reaction is allowed to proceed for 15 minutes at 37° C. and is terminated by the addition of an equal amount of cold 5% trichloroacetic acid. After centrifugation, an aliquot of the supernatant is placed on phosphocellulose filters (where the peptide binds through charge interactions) and rinsed with several washes of 75 mM phosphoric acid. The samples are quantitated by scintillation spectrometry.

Osteoblast Cell Proliferation

The action of select compounds to stimulate osteoblast growth can be measured in culture by assuming the rate of DNA synthesis is proportional to the rate of $^3H$-thymidine incorporation into DNA. Only cells undergoing mitosis will synthesize new DNA and thus only these cells will incorporate the radiolabelled DNA-specific thymidine. The stimulation of the proliferation and differentiation of bone-forming cells, osteoblasts, is a prerequisite for an increase in bone formation and bone mass. The ability of agents to increase osteoblast proliferation and differentiation can be predicted (reference) by their action on cultured osteoblast-line cells in vitro. In this test human TE85 osteoblast-line cells (100,000) were plated on 24 well plates in DMEM containing 5% fetal calf serum for 48 hours. After removal of the media, 0.3 mL of serum-free media containing 0.25% BSA was added to each well. After 24 hours, the treatments were added to the conditioned media for an additional 24 hours. Tritiated thymidine (0.6uCi) was added for the last two hours. After rinsing the cells with Dulbeccos PBS, the cells were released from the plate by trypsinizing with 0.25 mL trypsin (0.25%) for 5–10 min. An equal aliquot of 25% TCA was added and the cell lysate allowd to stand for 15 minutes at 4° C. The lysate was centrifuged for 10 minutes, the supernatant removed, and the pellet washed with 0.2 mL of cold 80% ethanol. After a second centrifugation, the pellet was suspended in 0.1 mL 0.1% Triton X-1 00. The pellet was then sonicated to remove all of the material from the sides of the tube. This material was placed into a scintillation vial. An additional 0.08 mL of the Triton was used to rinse the tube before placing into the vial. These mbined samples were quantitated by scintillation spectrometry.

TABLE 1

| EX# | TF85 $IC_{50}$ ($\mu M$) | Osteoblast Cell Prolif % X Control (concentration of drug, $\mu M$) |
|---|---|---|
| 2 | 35 | NT |
| 5 | 3 | NT |
| 7 | 30 | NT |
| 12 | 18 | 112.5 (100 $\mu M$) |
| 14 | 90% @ 300 $\mu M$ | NT |
| 15 | 33 | NT |
| 17 | 28 | 119 (100 $\mu M$) |
| 19 | 95% @ 300 $\mu M$ | NT |
| 20 | 2.4 | 139 (100 $\mu M$) |
| 22 | 14 | NT |
| 24 | 23 | NT |
| 26 | 5.8 | 138 (100 $\mu M$) |
| 28 | 6.3 | 111 (100 $\mu M$) |
| 29 | 9.4 | NT |
| 30 | 4.4 | NT |
| 31 | 0.82 | 159 (30 $\mu M$) |
| 32 | 73% @ 300 $\mu M$ | NT |
| 34 | 0.45 | 127 (100 $\mu M$) |
| 36 | 1.0 | NT |
| 38 | 1.0 | NT |
| 40 | 79% @ 300 $\mu M$ | NT |
| 43 | 1.0 | NT |
| 50 | 17 | NT |
| 52 | 30 | NT |
| 54 | 75% @ 30 $\mu M$ | NT |
| 56 | 30 | NT |
| 57 | 14 | NT |
| 58 | 5 | NT |
| 59 | 10 | NT |

NT = not tested

ENZYME ASSAY (CD45)

The compounds of the present invention also exhibit immunosuppressant activity as evidenced by the activity demonstrated by compounds of the present invention in the Enzyme Assay (CD 45) which is predictive of immunosuppressent activity. Koretzky, G., Kohmetscher, M., Kadleck, T., and Weiss, A.; Restoration of T-Cell receptor-mediated signal transduction by Transfection of CD45 cDNA into a CD45-deficient variant of the Jurkat T-Cell Line. *Journal of Immunology* 149 1138–1142 (1992). Peyron, J. F., Verma, S., Malefyt, R., Sancho, J., Terhorst, C., and Spits, H.; The CD45 Protein Tyrosine Phosphatase is Required for the Completion of the Activation Program Leading to Lymphokine Production in the Jurkat Human T-Cell Line. *Intern. Immunol.* 3, 1357–1366 (1991).

The assay is performed in microtubes with 500 uL incubation volumes. Into each micrtube is placed 350 uL of buffer (100 mM acetate pH 6.0), 50 uL of drug solution, enzyme and substrate (50 uL of 100 uM O-phospho-L-Tyrosine solution spiked with enough $^{14}$C-L-Tyrosine phosphate to give 44,000 counts per sample). The enzyme is derived from Jurkat cell (JEG-6) membranes. The microtubes are incubated for 90 minutes at 37° C. The reaction is stopped by placing the tubes on ice and adding 100 uL of quench buffer(1.1 mM of Sodium Orthovanadate and 0.55 uM of Sodium Fluoride). The samples are then passed over a 25 mM resin column (#AG1-X8) and allowed to drain into scintillation vials. Columns are then washed with 4 mls of distilled water. An additional 12 mls of Ecolume is added to each vial and the radioactivity is quantified by scintillation spectrometry. Compounds with activity at 300 μm or less are considered active immunosuppresant agents.

TABLE 2

| EX | IC$_{50}$ (CD45) (μM) |
|---|---|
| 2 | 20 |
| 5 | 7.5 |
| 12 | 14 |
| 19 | 28 |
| 22 | 1.0 |
| 26 | 1.2 |
| 28 | 6.0 |
| 40 | 38 |

To prepare the pharmaceutical compositions of this invention, a compound of formula 1, as the active ingredient is mixed with a pharmaceutical carrier according to conventional pharmaceutical compounding techniques, which carrier may take a wide variety of forms depending on the form of preparation desired for administration, e.g.; oral, by suppositories, injectable, or parenteral. In preparing the compositions in oral dosage form, any of the usual pharmaceutical media may be employed. Thus, for liquid oral preparations, such as, for example; suspensions, elixirs and solutions, suitable carriers and additives include water, glycols, oil, alcohols, flavorants, preservatives, coloring agents and the like. For solid oral preparations such as, for example; powders, capsules and tablets, suitable carriers and additives include, starches, sugars, diluents, granulating agents, lubricants, binders, disintegrating agents, and the like. Because of their ease of administration, tablets and capsules represent the most advantageous oral dosage unit form in which case, solid pharmaceutical carriers are obviously employed. If desired, tablets may be sugar coated or enteric coated by standard techniques. For suppositories, a suitable carrier cocoa butter may be used. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per unit dosage unit, e.g., tablet, capsule, powder, injection, suppository, teaspoonful and the like, from about 0.001 mg to 50 mg/kg. The dosages however, may be varied depending upon the physical condition of the patients, the severity of the condition being treated and the compound being employed. The use of either daily administration or post-periodic dosing may be employed.

EXAMPLES

The following examples describe the invention in greater detail and are intended to illustrate the invention but not to limit it. All examples given have been characterized by 300 MHz $^1$H NMR (reported as ppm downfield from tetramethylsilane) and by Mass Spectra (DCI or FAB) evaluation.

Each compound has satisfactory C,H,N elemental analysis within ±0.4% of theoretical values. The reactions described in the examples were run under a blanket of nitrogen. Unless noted, starting materials used in the examples were obtained from commercial sources, synthesized using cited literature methodology, or if new, described as an example in the invention.

The following examples further illustrate the present invention:

Example 1

O,O-Diethyl (2-chloro-5-nitro)phenylhydroxylmethylphosphonate

2-Chloro-5-nitrobenzaldehyde (2.40 g, 13.0 mmol) was mixed with diethylphosphite (1.67 mL, 13.0 mmol) and methanol (2 mL) and was heated to give a clear solution which was adsorbed onto basic alumina and allowed to stand overnight at room temperature. The product was then extracted with 30 methylene chloride-methanol 9:1 and evaporated to give a solid (3.35 g, 80.0%). mp 117–118.5° C. $^1$H NMR (DMSO): d 5.36 (dd,1H,PCH), 4.02 (m,4H, OCH$_2$), 1.20 (dt,6H,CH$_3$). MS (DCI): 324 (MH$_+$). C$_{11}$H$_{15}$ClNO$_6$P Example 2

(2-Chloro-5-nitro)phenylhydroxymethylphosphonic acid

The ester from example 1 (3.34 g,10.3 mmol) was dissolved in methylene chloride (100 mL) and bromotrimethylsilane (5.45 mL, 41.0 mmol) was added. The mixture was allowed to stand under nitrogen for 3.5 hours and was coevaporated with ethanol to give an oil which was dissolved in ether. Cyclohexylamine (1.18 mL, 10.3 mmol) was added and the product crystallized as the cyclohexylamine salt. An analytical sample was recrystallized from ethanol to give 1.30 g, 34.0%; mp 220° C.$^1$H NMR (DMSO): d, 8.49 (s,1H), 8.02 (d,1H), 7.60 (d,1H), 4.98 (d,1H,PCH). MS (DCl): 268 (MH$_+$). C$_{11}$H$_7$ClNO$_6$P/C$_6$H$_{13}$N Example 3

2-Azido-5-nitrobenzaldehyde

2-Chloro-5-nitrobenzaldehyde (2.81 g, 15.1 mmol) was dissolved in DMF (75 mL). To this was added sodium azide (1.18 g, 18.2 mmol). This was heated to 60° C. for 15 minutes before being poured onto ice. The solid was filtered and subsequently recrystallized from ethanol-water to give 2.12 g,73.0% of product. mp 91–92° C. IR (KBr) 2130 (azide); MS (DCl) 150 (M-azide). C$_7$H$_4$N$_4$O$_3$

Example 4

O,O-Diethyl-(2-azido-5-nitro)phenylhydroxymethylphosphonate

The aldehyde from example 3 (2.12 g, 11.0 mmol) was mixed with diethylphosphite (1.50 mL, 12.0 mmol) and methylene chloride (2 mL). This was mixed with basic alumina and allowed to stand overnight. The product was extracted with methylene chloride-methanol 19:1. Evaporation gave a solid (2.65 g, 73.0%); mp 143.4–144° C. $^1$H NMR (DMSO): d, 5.17 (dd,1H,PCH); MS (DCl): 331 (MH$_+$). $C_{11}H_{15}N_4O_6P$

Example 5

(2-Azido-5-nitro)phenylhydroxymethylphosphonic acid

The ester from example 4 (2.65 g, 8.02 mmol) was dissolved in methylene chloride (75 mL). Bromotrimethylsilane (5.30 mL, 41.0 mmol) was added and the mixture was allowed to stand overnight. The mixture was evaporated then redissolved in ethanol-ether 1:1. Addition of cyclohexylamine gave the crystalline cyclohexylamine salt. Recrystallization from ethanol gave 1.28 g, 43.0%; mp 190° C.$^1$H NMR (DMSO): d.4.82 (d,1H,PCH); IR (KBr) 2126 (azide). $C_7H_7N_4O_6P/C_6H_{13}N$

Example 6

O,O-Diethyl-(2,hydroxy-5-nitro)phenylhydroxymethylphosphonate

2-Hydroxy-5-nitrobenzaldehyde (2.96 grams,18.0 mmol) was dissolved in methylene chloride (10 mL) and mixed with diethylphosphite (2.30 mL, 18.0 mmol) and adsorbed onto basic alumina allowing the mixture to stand for 72 hours. The product was extracted with methylene chloride-methanol 19:1 and then purified on a silica gel column that was eluted with ethyl acetate-methylenechloride 1:1 to give an oil (3.66 g, 67.0%). $^1$ H NMR (DMSO): d, 5.26 (d,1H, PCH), 4.00 (m,4H,CH$_2$). MS (DCI): 306 (MH$_+$). $C_{11}H_{16}NO_7P$.

Example 7

(2-Hydroxy-5-nitro)phenylhydroxymethylphosphonic acid

The ester from example 6 (3.65 g, 12.0 mmol) was dissolved in methylene chloride. Bromotrimethylsilane (10.0 mL, 76.0 mmol) was added and this mixture was allowed to stand under nitrogen overnight. The mixture was then evaporated and redissolved in isopropanol-ether 1:1. Addition of cyclohexylamine formed a crude solid cyclohexylamine salt which was filtered and recrystallized from ethanol-ether to afford 2.12 g, 48.0%; mp 267° (dec). $^1$H NMR (DMSO): d,8.28 (S,1H), 7.93 (d,1H), 6.76 (d,1H), 4.65 (d,1H,PCH). MS (negFab): 247.8 (M-H). $C_7H_8NO_7P/C_6H_{13}N$.

Example 8

2-Fluoro-5-nitrophenylhydroxymethylphosphonic acid

2-Fluoro-5-nitrobenzaldehyde (1.75 g, 10.0 mmol) was dissolved in tetrahydrofuran(50 mL). Tris(trimethylsilyl)phosphite (3.45 mL, 10.0 mmol) was added. The reaction mixture was stirred for 2.5 hours. Evaporation gave an oil which was dissolved in ethanol-ether. Addition of cyclohexylamine (1.14 mL,10.0 mmol) gave a solid salt which was filtered. Recrystallization from water gave 1.88 g (53.0%) of analytically pure product, mp 226–231° C.$^1$H NMR (DMSO): d, 8.47 (m,1H), 8.11 (m,1H), 7.34 (t,1H), 4.85 (d,1H). MS (neg FAB): 249.9 (M-H). $C_7H_7FNO_6P/C_6H_{13}N$.

Example 9

2-Methoxy-5-nitrobenzaldehyde

2-Hydroxy-5-nitrobenzaldehyde (2.40 g, 14.0 mmol) was dissolved in dimethylformamide (50 mL). To this was added iodomethane (4.48 ml, 72.0 mmol) and sodium carbonate (3.04 g, 28.0 mmol). This mixture was stirred for 24 hours and was poured into water. The solid was collected by filtration to give 2.38 g (93.0%). Mp 88–89° C.;$^1$H NMR (CDCl$_3$): d, 10.46 (s,1H), 8.69 (d,1H), 8.45 (dd,1H), 7.15 (d,1H), 4.10 (s,3H). MS (DCl): 182 (MH$_+$). $C_8H_7NO_4$.

Example 10

(2-Methoxy-5-nitro)phenylhydroxymethylphosphonic acid

2-Methoxy-5-nitro benzaldehyde (2.38 g, .013.0 mmol) was dissolved in tetrahydrofuran (75 mL). Tris(trimethylsilyl)phosphite (4.40 mL, 13.0 mmol) was added. The reaction mixture was stirred for 72 hours after which time it was evaporated in vacuo to a residue which was redissolved in ethanol. Addition of cyclohexylamine (1.49 mL) gave 3.14 g, 67.0% of crystaline salt; mp 227–228° C. $^1$H NMR (acetic acid, d$_4$): d, 8.42 (t,1H, 8.16 (d,1H), 7.03 (d,1H), 5.48 (d,1H), 3.94 (s,3H). MS (neg FAB): 262 (M-1), 246 (M-OH). $C_8H_{10}NO_7P/C_6H_{13}N$.

Example 11

O,O-Diethyl-(2-phenoxy-5-nitro)phenythydroxy methylphosphonate

2-Chloro-5-nitrobenzaldehyde (2.56 g, 14.0 mmol) was dissolved in DMF (80 mL). Phenol (1.56 grams,17.0 mmol) and potassium hydroxide (1.0 g,17.8 mmol) were added. This mixture was heated at 110° C. for 1.5 hours and poured into water. The product was extracted from the mixture with ethyl acetate. The organic layer was dried and evaporated to give an oil which was immediately mixed with diethylphosphite (1.80 mL, 14.0 mmol) and excess basic alumina. This mixture stood overnight. Product was extracted from the alumina with methylene chloride and purified via silica gel column chromatography. Mobile phase consisted of a 1:1 mix of ethyl acetate-hexane then ethyl acetate giving 1.65 g (31%) of product. $^1$H NMR (CDCl$_3$): d, 5.75 (m,2H,PCH, OH), 4.20 (m,4H,CH$_2$). MS (DCl): 382 (MH$_+$). $C_{17}H_{20}NO_7P$.

Example 12

(2-Phenoxy-5-nitro)phenylhydroxymethylphosphonic acid

The ester of example 11 (1.62 g,4.25 mmol) was dissolved in methylene chloride (50 mL). Bromotrimethylsilane (2.80 mL, 22.0 mmoi) was added. After standing overnight, the reaction mixture was evaporated and the resultant oil redissolved in ethanol-ether, 1:1. Addition of propyleneoxide and 1.1 equivalents of cyclohexylamine yielded the crystalline salt, 1.27 g, 70.0%; mp 211–213° C. $^1$H NMR (DMSO): d, 5.10 (d,1H,PCH); MS (DCl) 244 (m-PO$_3$H$_2$). C$_{13}$H$_{12}$NO$_7$P/C$_6$H$_{13}$N.

Example 13

O,O-Diethyl [2-(4-methyl)phenoxy-5-nitro] phenylhydroxymethylphosphonate p-Cresol (2.08 g, 19.0 mmol) was dissolved in dimethylformamide and potassium hydroxide (1.1 g, 19.0 mmol) was added. This mixture was heated at 70° C. for 15 minutes before addition of 2-chloro-5-nitrobenzaldehyde (3.00 g, 16.0 mmol). The reaction mixture heated at 100° C. for 4 hours. The mixture was then poured onto ice and the product was extracted with ethyl acetate. The organic layer was washed with water, dried over magnesium sulfate and concentrated in vacuo to an oil which was immediately mixed with diethyl phosphite (2.06 mL, 16.0 mmol) and adsorbed onto excess basic alumina. After 16 hours, the product was extracted with methylene chloride and purified by silica gel column chromatography eluted with ethyl acetate-hexane 1:1 affording the product (2.16 g, 34.0%) as an oil. $^1$H NMR (CDCl$_3$): d, 5.70 (dd,1H,PCH), 2.35 (s,3H,CH$_3$). MS (DCl): 396 (MH$_+$). C$_{18}$H$_{22}$NO$_7$P.

Example 14

[2-(4-Methyl)phenoxy-5-nitro]phenylhydroxymethyl phosphonic acid

The ester from example 13 (2.16 g, 5.50 mmol) was dissolved in methylene chloride. Bromotrimethylsilane (3.60 mL, 27.0 mmol) was added and the mixture was stirred for 4 hours. The reaction mixture was then evaporated and the resulting oil was dissolved in ethanol-ether, 1:1. Addition of propylene oxide and 1.1 equivalents of cyclohexylamine resulted in a solid salt which was filtered giving 1.42 g (59.0%); mp 175–176° C. $^1$H NMR (DMSO): d, 5.05 (d,1H, PCH), 2.31 (s,3H,CH$_3$). MS (DCl): 339 MH$_+$). C$_{14}$H$_{14}$NO$_7$P/C$_6$H$_{13}$N.

Example 15

[2-(3-Pyridyl)oxy-5-nitro]phenylhydroxymethyl-phosphonic acid

3-Hydroxypyridine (1.81 g, 19.0 mmol) was dissolved in dimethylformamide. Potassium hydroxide (1.1 g) was added and the mixture was heated to 70° C. for 15 minutes before adding 2-chloro-5-nitrobenzaldehyde (3.00 g, 16.0 mmol). The reaction mixture was stirred at 100° C. for 5 hours before being poured onto ice. The product was extracted with ethyl acetate. The organic layer was washed with water and dried over magnesium sulfate. Evaporation in vacuo gave an oil which was purified by column chromatography on silica gel column eluded with ethyl acetate-hexane, 1:1 giving 1.53 g (39%) of 2-(3-pyridyl)oxy-5-nitrobenzaldehyde. $^1$H NMR (CDCl3): d, 10.62 (s,1H, CHO). A solution of 1.45 g, (5.94 mmol) of 2-(3-pyridyl) oxy-5-nitrobenzaldehyde in tetrahydrofuran was reacted with tris(trimethylsilyl)phosphite (2.00 mL, 6.00 mmol) for 16 hours. Evaporation in vacuo gave an oil which was crystallized from ethanol to give 1.02 g (52%); mp 255–257° C. $^1$H NMR (DMSO): d 5.57 (d,1H,PCH): MS (DCl): 327 (MH$_+$). C$_{12}$H$_{11}$N$_2$O$_7$P.

Example 16

O,O-Diethyl-(2-phenylthio-5-nitro) phenylhydroxymethylphosphonate

2-Chloro-5-nitrobenzaldehyde (3.62 g, 15.6 mmol) was dissolved in DMF. To this was added potassium hydroxide (1.12 g) and thiophenol (2.00 mL, 20.0 mmol). This mixture was heated to 100° C. for 45 minutes and then poured onto crushed ice. The product was extracted with ethyl acetate. The organic layer was dried over magnesium sulfate and evaporated to a red oil which was immediately mixed with diethylphosphite (2.00 mL,15.6 mmol) and basic alumina. This stood for sixteen hours. The product was extracted with methylene chloride and concentrated in vacuo. The resulting oil crystallized from ethyl acetate to give 3.70 g (60.0%). mp 146.5–147.5° C. $^1$H NMR (CDCl$_3$): d, 5.78 (m,2H,OH, PCH), 4.23 (m,4H,CH$_2$): MS (DCl): 398 (MH$_+$). C$_{17}$H$_{20}$NO$_6$PS.

Example 17

(2-Phenylthio-5-nitro) phenylhydroxymethylphosphonic acid

The ester from example 16 (3.68 g, 9.26 mmol) was reacted with bromotrimethylsilane (4.89 mL, 37.0 mmol) in methylene chloride for four hours. The mixture was then evaporated and dissolved in ethanol. Addition of cyclohexylamine caused a solid salt to form which was filtered and recrystallized from ethanol yielding 1.48 g (36%); mp 229–231° C. $^1$H NMR (DMSO): d, 5.15 (d,1H,PCH). MS (neg FAB) 340 (M-1). C$_{13}$H$_{12}$NO$_6$PS.

Example 18

O,O-Diethyl-[2-(4-chlorophenylthio)-5-nitro] phenylhydroxymethylphosphonate 2-(4-Chlorophenylthio)-5-nitrobenzaldehyde (3.10 g, 106 mmol) was mixed with diethyl phosphite (1.5 mL, 11.6 mmol) and methylene chloride (5 mls). This was adsorbed onto excess basic alumina and allowed to stand overnight. Product was extracted with methylene chloride and evaporated to give a solid which was triturated with ether. The crystalline product was collected by filtration giving 3.18 g (70.0%). Mp 144° C.; $^1$H NMR (DMSO): d, 5.50 (dd,1H, PCH). MS (DCl): 432 (MH$_+$). C$_{17}$H$_{19}$ClNO$_6$PS.

Example 19

[2-(4-Chlorophenylthio)-5-nitro] phenylhydroxymethylphosphonic acid

The ester from example 18 (3.16 g, 7.32 mmol) was reacted with bromotrimethylsilane (3.86 mL, 29.0 mmol) in 100 mL of methylene chloride at room temperature for 4.5 hours. Evaporation of the gave a crude oil which was coevaporated with ethanol then resolvated in ethanol-ether 1:1. Addition of cyclohexylamine caused the product to crystallize. The solid was filtered and recrystallized from ethanol To give 1.18 grams (34%). Mp 229–232° C.; $^1$H NMR (DMSO) d 5.15 (d,1H,PCH); MS (neg FAB) 374 (M-H). C$_{13}$H$_{11}$ClNO$_6$PS/C$_6$H$_{13}$N.

Example 20

[2-(3-Trifluoromethyl)phenylthio-5-nitro] phenylhydroxymethylphosphonic acid

3-Trifluoromethylthiophenol (1.86 g, 9.90 mmol) was dissolved in dimethylformamide. To this was added 2-chloro-5-nitro benzaldehyde (1.84 g, 9.90 mmol) and sodium carbonate (1.17 g, 11.0 mmol). This was heated to 100° C. for 2.5 hours before being poured onto ice. The product was extracted with ethyl acetate and the organic layer was washed with water, dried over magnesium sulfate and concentrated in vacuo to an oil (3.04 g, 94.0%) which was dissolved in 80 mL of tetrahydrofuran. Tris(Trimethylsilyl)phosphite (3.10 mL, 9.29 mmol) was added and the reaction was stirred for 3 hours before being evaporated in vacuo. The crude oil obtained was dissolved in ethanol-ether,1:1 and addition of excess cyclohexylamine gave crystalline salt; 2.83 g (59.0%) which yielded the analytical sample by recrystallization from ethanol-ether, mp 203–206° C.; $^1$H NMR (DMSO): d, 8.50 (s, 1H,) 7.93 (d,1H), 7.67 (m,4H), 7.20 (d,1H),5.18 (d,1H,PCH). MS (neg FAB): 424 (M-H). $C_{14}H_{11}F_3NO_6PS/C_6H_{13}N$.

Example 21

O,O-Diethyl-[2-(2-pyridyl)thio-5-nitro]phenylhydroxymethylphosphonate

A mixture of 2-(2-pyridylthio)-5-nitrobenzaldehyde (3.02 g,11.6 mmol), diethylphosphite (1.50 mL, 11.6 mmol), and methylene chloride (5 mls) was adsorbed onto excess basic alumina and was allowed to stand for 20 hours. The product was extracted with methylene chloride and purified on a silica gel column eluting with methylene chloride-methanol, 19:1. Evaporation of the solvents gave a solid (3.68 g, 80.0%), mp 114° C. $^1$H NMR (CDCl$_3$): d, 5.70 (dd,1H, PCH), 4.15 (m,4H,CH$_2$). MS (DCl): 399(MH$_+$). $C_{16}H_{19}N_2O_6PS$.

Example 22

[2-(2-Pyridyl)thio-5-nitro]phenylhydroxymethylphosphonic acid

The ester from example 21 (3.64 g, 9.15 mmol) was reacted with bromotrimethylsilane (4.83mL,37.0 mmol) in methylene chloride under nitrogen for 16 hours. Evaporation in vacuo gave an oil which was coevaporated with methanol to a residue which solidified upon addition of water to give 2.68 g (86.0%), mp 219–220° C.$^1$H NMR (DMSO): d, 5.35 (d,1H,PCH). MS (DCl): 261 (M-PO$_3$H$_2$). $C_{12}H_{11}N_2O_6P$.

Example 23

O,O-Diethyl-[2-(2-methoxyphenylthio)-5-nitro]phenylhydroxymethylphosphonate

2-Chloro-5-nitrobenzaldehyde (3.08 g, 17.0 mmol) was dissolved in dimethylformamide. 2-Methoxybenzenethiol (2.62 g, 19.0 mmol) and potassium hydroxide (1.05 g) were added. This mixture was heated at 110° C. for 15 minutes and was then diluted with water. The product extracted with ethyl acetate which was dried over magnesium sulfate and concentrated in vacuo to a solid which was immediately mixed with diethylphosphite (2.20 mL, 17.0 mmol), methylene chloride (5 mL) and adsorbed onto excess basic alumina. After 20 hours at room temperature, the product was extracted with methylene chloride and column chromatographed (silica gel) with ethyl acetate-hexane 2:1. Fractions were evaporated to give a solid which was triturated with ether and collected to give 3.10 g (53.0%) of the ester. mp 158–161° C.$^1$H NMR (DMSO): d, 5.50 (dd,1H, PCH), 3.76 (s,3H,OCH$_3$). MS (DCl): 428 (MH$_+$). $C_{18}H_{22}NO_7PS$.

Example 24

[2-(2-Methoxyphenylthio)-5-nitro]phenylhydroxymethylphosphonic acid

The ester from example 23 (3.08 g, 7.21 mmol) was reacted with bromotrimethylsilane (4.80 mL, 36.0 mmol) in methylene chloride (100 mL) under nitrogen overnight. The mixture was then evaporated and redissolved in ethanol. Addition of excess cyclohexylamine gave 2.70 g, (80%) of crystalline salt, mp 205–208° C.$^1$H NMR (DMSO): d, 8.48 (t,1H), 7.92 (d,1H), 7.36 (t,1H), 7.10d,1H), 6.97 (m,3H), 5.17 (d,1H,PCH), 3.76 (s,3H,CH$_3$). MS (neg FAB): 369 (M-H). $C_{14}H_{14}NO_7PS/C_6H_{13}N$.

Example 25

O,O-Diethyl-(2-cyclohexylthio-5-nitro)phenylhydroxymethylphosphonate

2-Cyclohexylthio-5-nitrobenzaldehyde (2.43 g, 9.16 mmol) was mixed with diethyl phosphite (2.0 mL), methanol (5 mL) and adsorbed onto excess basic alumina and allowed to stand for 16 hours. Product extracted with methylene chloride and purified by column chromatography (silica gel) with ethyl acetate-hexane, 1:1. Evaporation of appropriate fractions gave 2.56 g (69%) of a white solid, mp 145–146° C. $^1$H NMR (CDCl3): d, 5.80 (dd,1H,PCH) 4.08(m,4H,OCH$_2$). MS (DCl): 404 (MH$_+$). $C_{17}H_{26}NO_6PS$.

Example 26

(2-Cyclohexylthio-5-nitro)phenylhydroxymethylphosphonic acid

The ester from example 25 (2.55 g, 6.32 mmol) was reacted with bromotrimethylsilane (4.20 mL, 32.0 mmol) in methylene chloride (100 mis) under nitrogen for 3 hours. The mixture was then evaporated and redissolved in ethanol. Addition of propylene oxide and excess cyclohexylamine gave a solid which was filtered yielding 2.49 g, (91%) of cyclohexylammonium salt, mp 222–224° C.$^1$H NMR (DMSO): d, 8.45 (s,1H,ArH), 7.95 (d,1H,ArH), 7.58 (d,1H, ArH) 5.05 (s,1H,PCH). MS (DCl):346 (M-H). $C_{13}H_{18}NO_6PS/C_6H_{13}N$.

Example 27

O,O-Diethyl-(2-benzylthio-5-nitro)phenylhydroxymethylphosphonate 2-benzylthio-5-nitrobenzaldehyde (2.64 g, 9.66 mmol) was mixed with diethylphosphite (1.50 mL,11.6 mmol), methylene chloride (5 mL) and adsorbed onto excess basic alumina and allowed to stand overnight. Product was extracted with methylene chloride and evaporated to give an oil which solidified. The solid was triturated with ether and filtered yield, 2.92 grams (73%) mp 107.5–109° C. $^1$H NMR ( CDCl3): d, 5.70 (d,1H,PCH). MS (DCl): 412 (MH$_+$). $C_{18}H_{22}NO_6PS$.

Example 28

(2-Benzylthio-5-nitro)phenylhydroxymethylphosphonic acid

The ester from example 27 (2.90 g, 7.05 mmol) was dissolved in 80 mis of methylene chloride, bromotrimethylsilane (4.65 mL, 35.0 mmol) was added and allowed to stand under nitrogen for 4 hours. This mixture was coevaporated with ethanol-water and redissolved in ethanol. Addition of excess propylene oxide and cyclohexylamine gave 1.74 g (54%) of crystalline product as its cyclohexylammonium salt, mp 219–222° C. $^1$H NMR (DMSO-D6): d, 5.00 (d,1H,PCH) 4.35 (dd,2H,CH$_2$); MS (neg FAB) 354 (M-H). $C_{14}H_{14}NO_6PS/C_6H_{13}N$.

Example 29

[2-(2-Methyl)benzylthio-5-nitro]phenylhydroxymethyl phosphonic acid

2-Chloro-5-nitrobenzaldehyde (2.23 g, 12.0 mmol) was dissolved in 75 mL of dimethylformamide. To this solution was added 2-methylbenzylthiol (1.66 g,12.0 mmol) and potassium hydroxide (0.85 g). This mixture was heated at 100° C. for 25 minutes and then was poured into water. The product was extracted with ethyl acetate (200 mL). The organic layer was washed with water, dried over magnesium sulfate and evaporated to give 2.96 g (86%) of [2-(2-methyl) benzylthio]-5-nitrobenzaldehyde which was immediately reacted with tris(trimethylsilyl)phosphite (3.44 mL,10.3 mmol) in tetrahydrofuran for 2.5 hours. Evaporation of the reaction mixture gave a residual oil which was dissolved in ethanol-ether, 1:1. Addition of cyclohexylamine (1.18 mL, 10.3 mmol) gave 1.45 g (30.0%) of the crystalline salt. An analytical sample was prepared by recrystallization from ethanol. $^1$H NMR (DMSO-D6): d, 8.39 (s,1H), 7.97 (d,1H), 7 60 (d,1H), 7.34 (d,1H), 7.15 (m,3H), 4.97 (d,1H,PCH), 4.30 (dd,2H,CH$_2$), 2.38 (s,3H,CH$_3$). MS (neg FAB): 368 (M-H). $C_{15}H_{16}NO_6PS/C_6H_{13}N$.

Example 30

[2-(3-Methyl)benzylthio-5-nitro] phenylhydroxymethyl phosphonic acid

2-Chloro-5-nitrobenzaldehyde (3.53 g, 19.0 mmol) was dissolved in 80 mL of DMF. To this solution was added potassium hydroxide (1.20 g) and 3-methylbenzylthiol (2.67 g, 19.0 mmol). The resultant mixture was heated at 100° C. for 30 minutes, poured into water and extracted with ethyl acetate. The organic layer was washed with water, dried over magnesium sulfate and evaporated in vacuo to a crude solid (4.92 g, 89.0%). The solid was dissolved in tetrahydrofuran and tris(trimethylsilyl)phosphite (5.72 mL, 17.0 mmol) was added. After 3 hours, the reaction mixture was evaporated in vacuo to an oil which was dissolved in ethanol-ether 1:1. Addition of cyclohexylamine (1.94 mL, 19.0 mmol) caused a solid to form. This was filtered to give 1.70 g (21.4%) which was recrystallized from methanol-ether to give the analytical sample, mp 195–196° C.$^1$H NMR (DMSO): d, 8.39 (s,1H), 7.95 (d,1H), 7.55 (d,1H), 7.23 (m,3H), 7.07 m,1H), 4.97 (d,1H,PCH), 4.30 (dd,2H,CH$_2$), 2.28 (s,3H, CH$_3$). MS (neg FAB): 368 (M-H). $C_{15}H_{16}NO_6PS/C_6H_{13}N$.

Example 31

[2-(4-Methyl)benzylthio-5-nitro] phenylhydroxymethylphosphonic acid

2-Chloro-5-nitrobenzaldehyde (2.10 g, 11.0 mmol) was reacted with 4-methylbenzylthiol (1.57 g, 11.0 mmol) and potassiuim hydroxide (0.77 g) in 80 mL of dimethylformamide at 100° C. for 45 minutes. The mixture was then poured into water and extracted with ethyl acetate. The organic layer was washed with water, dried over magnesium sulfate, and evaporated to give an oil (3.00 g, 89.0%). The crude product was dissolved in tetrahydrofuran and tris (trimethylsilyl)phosphite (3.50 mL, 10.0 mmol) was added. The resultant reaction mixture was stirred for 3.5 hours at room temperature and then evaporated in vacuo to a residual oil. The oily acid was converted to 2.30 g (49.0%) of crystalline salt with cyclohexylamine (1.14 mL, 10.0 mmol). An analytical sample obtained by recrystallization from ethanol, mp 207–209° C. $^1$H NMR (DMSO-D6): d, 8.38 (s,1H), 7.95 (d,1H), 7.55 (d,1H), 7.30 (d,2H), 7.12 (d,2H), 4.97 (d,1H), 4.28 (dd,2H), 2.25 (s,3H). MS (neg FAB): 368 (M-H). $C_{15}H_{16}NO_6PS/C_6H_{13}N$.

Example 32

[2-(4-Methylphenylethylthio)-5-nitro]phenyl-hydroxymethyl phosphonic acid

4-Methylphenylethylmercaptan (2.0 g, 13.0 mmol) was dissolved in 100 ml of dimethylformamide. Potassium hydroxide (0.75 g) was added and the resultant mixture was heated at 70° C. for a 0.5 hour before adding 2-chloro-5-nitro benzaldehyde (2.20 g, 12.0 mmol). The reaction was allowed to stir at 70° for 16 hours after which time the mixture was poured onto ice. The product extracted with ethyl acetate. The organic layer was washed with water, dried over magnesium sulfate and concentrated to give an oil (3.50 g). This oil was immediately dissolved in tetrahydrofuran (50 mL) tris(trimethylsilyl)phosphite (3.4 mL,12.0 m mol) was added. The reaction was stirred for 16 hours, evaporated in vacuo, and redissolved in ethanol. Addition of cyclohexylamine (1.1 mL, 10.0 mmol) gave crystalline product as its salt. The crude solid was recrystallized from ethanol-ether to give 220 mg, (4.50%) of the desired product. Mp 223–225° C. $^1$H NMR (DMSO-D6): d, 4.95 (d,1H, PCH), 3.25 (t,2H,SCH$_2$), 2.85 (t,2H,CH$_2$). MS (neg APCl): 382 (M-H). $C_{16}H_{18}NO_6PS/C_6H_{13}N$.

Example 33

2-(3-Phenylpropyl)thio-5-nitrobenzaldehyde

To a reaction mixture of DMF (40 mL), potassium hydroxide (1.45 g, 25.9 mmol), and 3-phenylpropyl mercaptan (3.28 g, 21.6 mmol), was added 2-chloro-5-nitrobenzaldehyde (4.00 g, 21.6 mmol). The resulting mixture was heated at 100° C. for 45 minutes. The mixture was cooled, poured onto ice-water (350 mL) and allowed to stand at room temperature for 48 hours. A yellow semi-solid which formed was collected and dissolved in ethyl acetate (100 mL), dried over Na$_2$SO$_4$, and filtered. The solvent removed by evaporation to give a dark yellow gum, 6.71 g.$^1$H NMR (CDCl$_3$): d, 10.27 (s,1H,CHO). MS (DCl): 302 (MH$_+$). The crude product was carried on without further purification in example 34. $C_{16}H_{15}NO_3S$.

Example 34

[2-(3-Phenylpropyl)thio-5-nitro]phenylhydroxy-methyl phosphonic acid

A solution of 2-(3-phenylpropyl)thio-5-nitrobenzaldehyde (6.50 g, 21.6 mmol) in tetrahydrofuran (40 mL), under N$_2$, was treated with tris(trimethylsilyl) phosphite (7.21 mL ,21.6 mmol) and the resulting solution was stirred at room temperature for 3 days. The reaction mixture was concentrated to dryness and the residue was dissolved in ethanol (40 mL). The resulting yellow solution was treated with cyclohexylamine (2.47 mL, 21.6 mM) and a yellow precipitate formed. which collected by filtration, washed with absolute ethanol, (60 mL). and recrystallized from ethanol-water to give 3.52 g (33.8%) of analytically pure yellow solid, mp 194–206° C. $^1$H NMR (CD$_3$COOD): d, 5.59 (d,1H,PCH), 3.06 (t, 2H, SCH$_2$), 2.78 (t, 2H, PhCH$_2$). MS (neg FAB): 382(M-H). $C_{16}H_{18}NO_6PS/C_6H_{13}N$.

Example 35

2-(1-Decane)thio-5-nitrobenzaldehyde

DMF (40 mL) was added to KOH (1.49 g, 56.11 mmol), under N$_2$, and to the resulting mixture was added 1-decanethiol (4.47 mL, 21.6 mmol). After 10 minutes, 2-chloro-5-nitrobenzaldehyde (4.00 g, 21.6 mmol). was added and the reaction mixture was heated at 100° C. for 45 minutes. The mixture was cooled, poured onto ice, and the liquid was decanted from the resulting gummy semi-solid which formed. The residue was dissolved in ethyl acetate (125 mL), dried ($Na_2SO_4$), filtered, and concentrated to dryness to give a dark yellow oil, 7.27 g, (41%). MS (DCl): 324 ($MH_+$). $C_{17}H_{23}NO_3S$. The crude product was carried on without purification in example 36.

Example 36

[2-(1-N-decyl)thio-5-nitro] phenylhydroxymethylphosphonic acid

A solution of 2-(1-n-decyl)thio-5-nitrobenzaldehyde (6.97 g, 21.6 mmol) in THF (40 mL), under $N_2$ was treated with tris(tri-methylsilyl)phosphite (7.21 mL, 21.6 mmol) and the resulting solution was stirred at room temperature for 18 hours. The reaction mixture was concentrated to dryness and the dark yellow oil obtained, was dissolved in ethanol (40 mL). The crude acid was converted to a crystalline salt with cyclohexylamine ( 2.47 mL, 21.6 mmol) and allowed to stand at room temperature for 2 hours. The solution was concentrated to dryness and the residue was recrystallized from ethanol-water to give a yellow solid, 3.40 g (39.0%), mp 213–222° C.$^1$H NMR (DMSO-$d_6$): d, 4.97 (d, 1H, PCH), 3.02 (t,2H, $SCH_2$), 0.850 (t, 3H, decyl-$CH_3$). MS (neg FAB): 404 (M-H). $C_{17}H_{28}NO_6PS$.

Example 37

2-(1-N-hexyl)thio-5-nitrobenzaldehyde

DMF (50 mL) was added to KOH (3.40 g, 60.59 mM), under $N_2$, and to the resulting mixture was added 1-hexanethiol (5.00 mL, 50.5 mmol). After 10 minutes, 2-chloro-5-nitrobenzaldehyde (9.37 g, 50.5 mmol) was added and the reaction mixture was heated at 100° C. for 45 minutes and then poured into ice-$H_2O$ (350 mL). The aqueous mixture was extracted with ethyl acetate (3 X 100 mL) and the solvent was evaporated in vacuo to yield a reddish oil. Water (500 mL) was added. The liquid was decanted and the red-brown gum which remained was dissolved in ethyl acetate (100 mL), dried ($Na_2SO_4$), filtered, and concentrated to dryness to give a brown gum, 13.1 g (97%). MS (DCl): 268 ($MH_+$). $C_{13}H_{17}NO_3S$. This gum was carried on without purification in example 38.

Example 38

[2-(1-N-hexanyl)thio-5-nitro]phenylhydroxymethylphosphonic acid

A solution of 2-(1 -hexylthio-5-nitrobenzaldehyde (13.1 g, 48.9 mmol) in THF (50 mL), under $N_2$, was treated with tris(tri-methylsilyl)phosphite (16.4 mL, 49.0 mmol) and the resulting solution was stirred at room temperature for 6 days. The reaction mixture was concentrated to dryness and the residual brown oil was dissolved in absolute ethanol (40 mL) and cyclohexylamine (5.60 mL, 49.0 mmol) was added. The solution was then concentrated to dryness and the residual yellow solid was recrystallized from ethanol-water to give a yellow solid, 9.81 g (57.0%). An analytical sample was prepared by further recrystallization from ethanol-water, mp 206–218° C. $^1$H NMR(DMSO-$d_6$): d, 4.99 (d,1H, , PCH), 3.03 (t. 2H, $SCH_2$), 0.858 (t, 3H, hexyl-$CH_3$). MS (neg FAB): 348(M-H). $C_{13}H_{20}NO_6PS/C_6H_{13}N$.

Example 39

O,O-Diethyl 2-nitro-4-thienylhydroxymethylphosphonate

A solution containing 2-nitro-4-thiophenecarboxaldehyde (2.61 g, 16.6 mmol), diethyl phosphite (2.14 mL, 16.6 mmol), and methanol (5 mls) was adsorbed onto excess basic alumina. After 16 hours the product was extracted with methylene chloride, concentrated and purified by column chromatography (silica gel). Elution with methylene chloride-methanol 19:1 gave the product (3.55 g) as an oil. $^1$ H NMR (CDC13): d, 5.05 (dd,1H,PCH), 4.15 (m,4H, $CH_2$), 1.33 (dt,6H,$CH_3$). MS (DCl): 296 ($MH_+$). $C_9H_{14}NO_6PS$.

Example 40

2-Nitro-4-thienylhydroxymethylphosphphonic acid

The ester from example 39 (3.50 g, 12.0 mmol) was dissolved in methylene chloride ( 75 mL). and bromotrimethylsilane (11.0 mL, 83.0 mmol) was added. After 3 hours, this mixture was evaporated and redissolved in ethanol-ether, 1:1. Addition of propylene oxide followed by excess cyclohexylamine gave the salt as an off-white solid. Recrystallization of the salt from ethanol-water gave 2.50 g (62.0%), mp 221–224° C.$^1$H NMR ($CD_3OD$): d, 8.15 (s,1H, Ar), 7.68 (s,1H,Ar), 4.77 (d,1H,PCH). MS (neg FAB): 238 (M-H). $C_5H_6NO_6PS/C_6H_{13}N$.

Example 41

O,O-Diethyl (4-nitro)-2-thienylhydroxymethylphosphonate

Thiophene-2-carboxaldehyde (3.20 mL, 34.0 mmol) was dissolved in sulfuric acid (20 mL) and cooled to 0° C. Potassium nitrate (4.05 g, 44.0 mmol) was added and the resultant mixture was stirred for 30 minutes and was poured onto ice. The product was extracted with ether, washed with aqueous sodium bicarbonate, dried with anhyrous magnesium sulfate and evaporated to give an oil which was immediately mixed with diethylphosphite (4.40 mL, 34.0 mmol) and adsorbed onto excess basic alumina. After 18 hours, the product was extracted with methylene chloride, concentrated in vacuo to an oil and purified by column chromatography (silica gel) with ethyl acetate-hexane 1:1 to give 1.01 g (10.0%) as an oil. $^1$H NMR (DMSO-D6): d, 8.64 (s,1H) 7.62 (s,1H) 6.95 (dd,1H,OH), 5.36 (dd,1H,PCH), 4.05 (m,4H,$CH_2$), 1.22 (t,6H,$CH_3$). MS (DCl): 296 ($MH_+$), 278 (M-OH). $C_9H_{14}NO_6PS$.

Example 42

(4-Nitro)-2-thienylhydroxymethylphosphonic acid

O,O-Diethyl (4-nitro)-2-thienylhydroxymethylphosphonate (4.85 g, 16.0 mmol) was dissolved in methylene chloride and bromotrimethylsilane (13.0 mL, 96.0 mmol) was added. The resultant mixture was allowed to stand for 3.5 hours. The reaction mixture was evaporated to a residue which was dissolved in methanol. Propylene oxide and cyclohexylamine (1.83 mL, 16.0 mmol) were added. The resulting white solid was filtered giving 3.71 g (69.0%), mp 232–234° C.$^1$H NMR (DMSO-D6): d, 8.53 (S,1H), 7.49 (S,1H), 4.69 (d,1H,PCH). MS (neg FAB); 238 (M-H), 222 (M-OH). $C_5H_6NO_6PS/C_6H_{13}N$.

Example 43

5-Nitro-2-thiophenehydroxymethylphosphonic acid

5-Nitro-2-thiophenecarboxaldehyde (1.81 g, 11.5 mmol) was dissolved in 50 mL of anhydrous THF. To this was added tris(trimethylsilyl)phosphite (3.84 mls, 11.5 mmol).

After 2.5 hours, the mixture was coevaporated with ethanol. Addition of cyclohexylamine (1.32 mL, 11.5 mmol) gave 2.35 g (60.0%) of crystalline cyclohexylammonium salt, mp 169° C., (dec). $^1$H NMR (CD$_3$COOD): d, 7.84 (d,1H), 7.10 (t,1H), 5.27 (d,1H). MS (neg FAB): 238 (M-H). C$_5$H$_6$NO$_6$PS/C$_6$H$_{13}$N.

Example 44

O,O-Diethyl (3-nitro-4-chloro)phenylhydroxymethyl phosphonate

3-Nitro-4-chlorobenzaldehyde (3.22 g, 17.4 mmol) was mixed with diethylphosphite (2.24 mL, 17.4 mmol) and basic alumina. This was allowed to stand overnight. Product was extracted with methylene chloride-methanol 9:1. Evaporation of the solvent gave a crude residue which was purified by column chromatography (silica gel) eluting with ethyl acetate-hexane 1:1. The desired fractions were evaporated to yield 3.20 g (57.0%) of desired product as an oil. $^1$H NMR (DMSO-D$_6$): d, 8.08 (s,1H), 7.77 (m,2H), 6.63(dd,OH), 5.20 (dd,1H,PCH), 4.02 (m,4H,CH$_2$), 1.18(t,6H,CH$_3$): MS (DCl): 324 (MH$_+$). C$_{11}$H$_{15}$ClNO$_6$P.

Example 45

(3-Nitro-4-chloro)phenylhydroxymethylphosphonic acid

The ester from example 44 (3.15 g, 9.73 mmol) was dissolved in methylene chloride and bromotrimethylsilane (5.13 mL, 39.0 mmol) was added. After standing at room temperature for 18 hours, the mixture was coevaporated with ethanol to give a crude oil as product purified as a crystalline cyclohexylammonium salt yielding 3.24 g (88.0 %), mp 148° C. $^1$H NMR (CD$_3$COOD): d, 8.03 (s,1H), 7.72 (d,1H), 7.56 (d,1H), 5.14 (d,1H,PCH). MS (DCl): 267 (MH). C$_7$H$_7$ClNO$_6$P/C$_6$H$_{13}$N.

Example 46

O,O -Diethyl (3-nitro-4-hydroxy) phenylhydroxymethyl phosphonate

3-Nitro-4-hydroxybenzaldehyde (2.80 g, 16.7 mmol) was mixed with diethylphosphite (2.20 mL, 17.0 mmol) and dimethylformamide was added to achieve solution. The mixture was then mixed with basic alumina and allowed to stand overnight. The product was extracted from the basic alumina with methylene chloride-methanol 19:1 and evaporated in vacuo. The crude oily product was partitioned between water and ethyl acetate. The organic layer was washed with water, dried over magnesium sulfate and concentrated. Column chromatography (silica gel) eluting with ethyl acetate gave the pure product (1.43 g, 28.0%) as an oil. $^1$NMR (DMSO-D6): d, 7.94 (d,1H), 7.60(d,d,1H), 7.14 (d,1H), 6.35 (dd,1H,OH), 5.01 (dd,1H,PCH), 3.97 (m,4H), 1.18 (m,6H). MS (DCl): 306 (MH$_+$), 288 (M-OH). C$_{11}$H$_{16}$NO$_7$P.

Example 47

(3-Nitro-4-hydroxy)phenylhydroxymethyl phosphonic acid

O,O-diethyl-(3-nitro-4-hydroxy)phenylhydroxymethylphosphonate (1.40 g, 4.59 mmol) was dissolved in 50 mL of methylene chloride and bromotrimethylsilane (2.50 mL, 19.0 mmol) was added. After 18 hours at room temperature, the mixture was coevaporated with methanol. The product was purified as the cyclohexylammonium salt using 0.53 mL (4.60 mmol) of cyclohexylamine. The crude product was recrystallized from ethanol-water to give 0.90 g (56.0%) of analytical material, mp 210–211° C. $^1$NMR (DMSO-D6): d, 7.84 (s,1H), 7.47 (d,1H), 6.96 (d,1H), 4.51 (d,1H). MS (DCl): 249 (MH$_+$). C$_7$H$_8$NO$_7$P/C$_6$H$_{13}$N.

Example 48

(3-Nitro-4-methoxy)benzaldehyde

3-Nitro-4-hydroxybenzaldehyde (1.37 g, 8.20mol) was dissolved in dimethylformamide and methyl iodide (2.55 mL, 41.0 mmol) and sodium carbonate (1.74 g, 164 mmol) were added. The reaction mixture was stirred for 20 hours at ambient temperature and then poured into water. The solid product (1.10 g, 74.0%) was filtered, mp 82° C. $^1$H NMR (CDCl$_3$): d, 9.94 (s,1H), 8.37 (d, 1H), 8.11 (dd,1H), 7.25 (d,1H), 4.07 (s,3H). MS (DCl): 182 (MH$_+$). C$_8$H$_7$NO$_4$.

Example 49

(3-Nitro-4-methoxy)phenylhydroxymethyl phosphonic acid

3-Nitro-4-methoxybenzaldehyde (1.09 g, 6.20 mmol) was dissolved in tetrahydrofuran and tris(trimethylsilyl) phosphite (2.01 mL, 6.20 mmol) was added. The resultant mixture was stirred for 4 hours and then evaporated in vacuo to yield an oil. The crude product was dissolved in ethanol and 6.20 mmol of cyclohexylamine gave 1.16 g (52.0%) of the crystalline salt, mp 216–219° C. $^1$H NMR (CD$_3$COOD): d, 7.93 (s,1H), 7.70 (d,1H), 7.16 (d,1H), 5.04 (d,1H,PCH), 3.94 (s,3H,CH$_3$). MS (neg FAB): 262 (M-H). C$_8$H$_{10}$NO$_7$P/C$_6$H$_{13}$N.

Example 50

3-Nitro-4-benzoyloxybenzaldehyde

To a solution of benzoyl chloride (2.50 mL, 20.0 mmol) in methylene chloride (100 mL) cooled at 0° C. was added 3-nitro-4-hydroxybenzaldehyde (3.00 g, 19.0 mmol) and triethylamine (2.80 mL, 20.0 mmol). After 1 hour the mixture was washed with water and concentrated to an oil, in vacuo. The product was crystallized from ethyl acetate-hexane giving 1.70 g (33.0%); mp110.5–112° C. $^1$H NMR (CDCl$_3$): 10.05 (s,1H,CHO), 8.59 (s,1H) 8.20 (m,3H), 7.62 (2,1H), 7.38 (m,3H). MS (DCl) 272 (MH$_+$). C$_{14}$H$_9$NO$_5$.

Example 51

(3-Nitro-4-benzoyloxy)phenylhydroxymethyphosphonic acid

3-Nitro-4-benzoyloxybenzaldehyde (1.70 g, 6.30 mmol) was dissolved in tetrahydrofuran. Tris(trimethylsilyl) phosphite (1.90 mL, 6.50 mmol) was added and the resultant mixture was allowed to stand at room temperature for 16 hours before being evaporated invacuo. The resulting oil was dissolved in ethanol and the product crystallized upon addition of cyclohexylamine giving 1.50 g (67.0%) of the cyclohexylammonium salt, mp 216–217° C. $^1$H NMR (DMSO-D$_6$): d, 4.75 (d,1H,PCH). MS (neg FAB): 352 (M-H). C$_{14}$H$_{12}$NO$_8$P/C$_6$H$_{13}$N.

Example 52

(3-Nitro-4-methyl)phenylhydroxymethyphosphonic acid

3-Nitro-4-methylbenzaldehyde (2.00 g, 12.0 mmol) was dissolved in tetrahydrofuran and tris(trimethylsilyl)

phosphite (3.48 mL,12.0 mmol) was added. The mixture was allowed to stand for 16 hours before it being evaporated in vacuo. The residue obtained was redissolved in ethanol and upon addition of 1 equivalent of cyclohexylamine a solid salt was obtained; yield, 2.47 g (60.0%), mp 244–245° C. $^1$H NMR (DMSO-D$_6$): d, 4.53 (d,1H,PCH), 2.45 (s,3H, CH$_3$). MS (neg FAB): 246 (M-H). C$_8$H$_{10}$NO$_6$P/C$_6$H$_{13}$N.

Example 53

O,O-Diethyl[3-nitro 4-(4-bromophenylthio)]-phenylhydroxymethylphosphonate

A slurry of 3-nitro-4-(4-bromophenylthio)benzaldehyde (5.00 g, 14.8 mmol) in diethyl phosphite (20 mL), under N$_2$, was treated with excess basic alumina and the mixture was heated at 100° C. for 3 hours. The mixture was cooled, filtered, and the insoluble material washed with methanol (50 mL) and CH$_2$Cl$_2$ (50 mL). The solvent was removed in vacuo to give a yellow gum. The crude product was chromatographed on a silica gel column and eluted with ethyl acetate to afford 6.38 g (90.6%) of the ester, mp 117–120° C. $^1$H NMR (CDCl$_3$): d, 5.05 (d,1H, PCH), 4.00–4.24 (m, 4H, OCH$_2$), 1.15–1.40 (m,6H, CH3). MS (DCl): 476(MH$^+$). C$_{17}$H$_{19}$BrNO$_6$PS.

Example 54

[3-Nitro-4-(4-bromophenylthio)] phenylhydroxymethylphosphonic acid

A solution of the above described ester (4.00 g, 8.40 mmol) in CH$_2$Cl$_2$ (50 mL), under N$_2$, was treated with bromotrimethylsilane (6.65 mL, 50.4 mM), and the resulting solution was stirred at ambient temperature for 4 hours. The solvent was removed in vacuo and the residue was dissolved in ethanol (50 mL)/H$_2$O (50 mL) and stirred at room temperature for 16 hours. The yellow solid which precipitated was collected, washed with water-ethanol, 1:1 and dried to give 3.32 g (91.4%), mp193–198° C. (dec.); $^1$H NMR (CD$_3$COOD): d, 5.22 (d,1H,PCH). MS (DCl): 338 (M$^+$-PO$_3$H$_2$). C$_{13}$H$_{11}$BrNO$_6$PS.

Example 55

O,O-Diethyl-3-nitro- 4-(3,4-dichlorobenzyloxy) phenylhydroxymethyl phosphonate

A slurry of 4-(3,4-dichlorobenzyloxy)-3-nitrobenzaldehyde (5.00 g, 15.3 mmol) in diethyl phosphite (20 mL), under N$_2$, was treated with excess basic alumina and the mixture was heated at 100° C. for 3 hours. The mixture was cooled, and the product extracted with methylene chloride and methanol. The solvent was removed in vacuo to give a white solid which was triturated in ethyl acetate and methylene chloride (1:1) and filtered to give product as a white solid, 6.52 g (91.0%). The analytical sample was prepared by recrystallization from 2-propanol, mp 150–154° C. $^1$H NMR (DMSO-D$_6$): d, 5.34 (s, 2H, CH$_2$O), 5.06 (dd,1H,PCH), 3.80–4.20 (m,4H, OCH$_2$), 0.96–1.37 (m,6H, 2-CH$_3$). MS (DCl): 464 (MH$^+$). C$_{18}$H$_{20}$Cl$_2$NO$_7$P.

Example 56

[3-Nitro-4-(3,4-dichlorobenzyloxy)] phenylhydroxymethylphosphonic acid

A solution of the above ester (example 55), (3.00 g, 6.46 mmol) in ethanolic concentrated hydrochloric acid ( 50 mL)/ 50 mL) was heated at 100° C. for 16 hours. Upon cooling, the solid which formed, was filtered, washed with H$_2$O (20 mL) and dried to give 0.834 g of a yellow solid which was recrystallized from ethanol-water to give a yellow solid, 0.440 g as product. The free acid was dissolved in ether (50 mL)/ethanol (25 mL) and cyclohexylamine (1.75 mmol) was added. Upon standing at room temperature for 1 hour, a yellow precipitate formed which was filtered and recrystallized from absolute ethanol to give 0.120 g (3.65%) of analytically pure product as a white solid, mp 212–214.5° C. $^1$H NMR (DMSO-d$_6$): d, 5.27 (s, 2H,CH$_2$O), 4.52 (d, $^1$H, PCH). MS(DCl): 326(M-PO$_3$H$_2$). C$_{14}$H$_{12}$Cl$_2$NO$_7$P/C$_6$H$_{13}$N.

Example 57

[4-(4-Cyanophenoxy)-5-nitro]phenylhydroxy methylphosphonic acid

4-Cyanophenol (2.26 g, 19.0 mmol) was dissolved in 100 mL of dimethylformamide. To this was added potassium hydroxide (1.10 g, 19.0 mmol). The resultant reaction mixture was heated at 70° C. for 15 minutes before adding 2-chloro-5-nitrobenzaldehyde (3.00 g, 16.0 mmol). The reaction was heated at 100° C. for 4 hours before being poured onto ice. The product was extracted with ethyl acetate. the extract was dried and evaporated to give an oil (3.00 g, 69.0%) which was dissolved in tetrahydrofuran and reacted with tris(trimethylsilyl)phosphite (3.25 mL, 11.0 mmol). After 5 hours at room temperature, the reaction mixture was evaporated in vacuo to give an oil which formed a solid cyclohexylammonium salt in ethanol. Recrystallization of the crude salt from ethanol gave 600 mg (12%) of the analytical sample, mp 224–225° C. $^1$H NMR (DMSO-D$_6$): d, 4.65 (d,1H,PCH). MS (negFAB): 349 (M-H). C$_{14}$H$_{11}$N$_2$O$_7$P/C$_6$H$_{13}$N.

Example 58

(2-Chloro-5-nitro)phenyloxomethylphosphonic acid

2-Chloro-5-nitrobenzoylchloride (3.93 g, 17.9 mol) was dissolved in anhydrous tetrahydrofuran and tris (trimethylsilyl)phosphite (6.0 mL, 18.0 mmol) was added. This mixture was stirred for 3 hours at ambient temperature and upon evaporation yielded an oil which was dissolved in ethanol-ether,1:1 and converted to its cyclohexylammonium salt; yield, 2.61 g (40.0%). An analytical sample was prepared by recrystallization from ethanol-water. mp 172° C. $^1$H NMR (DMSOD6): d, 9.09 (d,1H), 8.28 (dd,1H), 7.78 (d, 1H). MS (neg FAB): 264 (M-H). C$_7$H$_5$ClNO$_6$P/C$_6$H$_{13}$N.

Example 59

(2-Phenyl-5-nitro) phenylhydroxymethylphosphonic acid

To a solution of 2-Phenyl-5-nitrobenzaldehyde [Snieckus, Synthesis. 184–187 (1989)] (700 mg, 3.10 mmol) in tetrahydrofuran was added tris(trimethylsilyl)phosphite (0.90 mL, 3.20 mmol). After stirring the mixture for 17 hours, it was evaporated in vacuo to give the crude product. Conversion to its cyclohexylammonium salt gave a solid from ethanol to give 500 mg (36.0%) of product, mp 216–217° C. $^1$H NMR (DMSO-d$_6$): d, 8.72 (s,1H), 8.06 (dd,1H), 7.75 (dd,1H), 7.51–7.32 (m,5H), 4.62 (d,1H,PCH). MS (neg FAB): 308 (M-H). C$_{13}$H$_{12}$NO$_6$P/C$_6$H$_{13}$N.

What is claimed is:

1. A compound represented by the formula I:

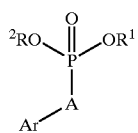

wherein Ar is selected from any of, 2-thienyl or 3-thienyl, each of which may be optionally substituted with Z;
wherein X and Y are each selected from any of H, halo, azido, phenyl, $O(CH_2)nR^3$, $S(O)_m(CH_2)_nR^3$, or $CH_2(CH_2)_nR^3$ wherein m=0–2, n=0–14, $R^3$=H, $C_1$–$C_4$ alkyl, $C_3$–$C_{10}$ cycloalkyl, pyridyl, aryl, substituted aryl wherein the aryl substituents are selected from any of $C_1$–$C_8$ alkyl, halo, carboxy, $C_1$–$C_4$ carboalkoxy, $C_1$–$C_4$ alkoxy, benzo, cyano, hydroxy, phenyl, phenoxy, nitro or trifluoromethyl, with the proviso that when Ar is phenyl, X is at the 2-position and Y is at the 4-position, wherein Z is selected from any of H, $C_1$–$C_4$ alkyl, $C_1$–$C_4$ alkoxy, cyano, halo, nitro, or trifluoromethyl;
wherein $R^1$ and $R^2$ are independently selected from any of H, $C_1$–$C_4$ alkyl, aralkyl, wherein the alkyl portion has 1–4 carbon atoms, substituted aralkyl wherein the aryl portion is independently substituted with any of halo, nitro, $C_1$–$C_4$ alkoxy or $C_1$–$C_4$ alkyl, $C_1$–$C_4$ alkylsulfonyl, phenylsulfonyl, substituted-phenylsulfonyl wherein the phenyl is independently substituted with any of $C_1$–$C_4$ alkyl or halo, $NR^3R^4$ wherein $R^3$ and $R^4$ are the same or different and are selected from either of H or $C_1$–$C_4$ alkyl;
wherein A is selected from any of $CHOR^5$ or C=O wherein $R^5$ is H, $C_1$–$C_4$ alkyl, $C_1$–$C_6$ acyl, benzoyl or substituted benzoyl wherein the substituents are any of halo or $C_1$–$C_4$ alkyl, or
the racemates, individual enantiomers, diastereomers when both stereogenic carbon and phosphorus atoms are present or pharmaceutically acceptable salts thereof.

2. The compound of claim 1, wherein Z is nitro.

3. The compound of claim 1, wherein Z is in (the 5-position when Ar is phenyl,) the 4 or 5 position when Ar is 2-thienyl and the 5-position when Ar is 3-thienyl.

4. The compound of claim 1, wherein $R^1$ and $R^2$ are both H.

5. A pharmaceutical composition comprising a therapeutically effective amount of a compound of claim 1 in combination with a pharmaceutically acceptable carrier.

6. A method of treating a bone wasting disease comprising administering a compound of claim 1 in an amount sufficient to treat such disease.

7. The method of claim 1, where the disease is osteoporis.

8. A method of suppressing the immune system of a patient comprising administering a therapeutically effective amount of the compound of claim 1 to the patient.

9. The compound of claim 1 wherein Ar is 2-thienyl.

10. The compound of claim 1 wherein Ar is 3-thienyl.

11. The compound of claim 9 wherein Z is nitro.

12. The compound of claim 10 wherein Z is nitro.

13. The compound of claim 1 wherein the compound is selected from:

5-nitro-2-thiophenehydroxymethylphosphonic acid;
4-nitro-2-thiophenehydroxymethylphosphonic acid;
5-nitro-3-thiophenehydroxymethylphosphonic acid;
2-nitro-4-thienylhydroxymethylphosphonic acid; O,O-diethyl (4-nitro)-2-thienylhydroxymethylphosphonate;
2-nitro-4-thienylhydropxymethylphosphonc acid;
(4-nitro)-2-thienylhydroxymethylphosphonic acid; and
O,O-diethyl 2-nitro-4-thienylhydroxymethylphosphonate.

* * * * *